(12) United States Patent
Obara et al.

(10) Patent No.: US 8,309,919 B2
(45) Date of Patent: Nov. 13, 2012

(54) INSPECTION METHOD FOR SEMICONDUCTOR WAFER AND APPARATUS FOR REVIEWING DEFECTS

(75) Inventors: Kenji Obara, Kawasaki (JP); Takehiro Hirai, Ushiku (JP)

(73) Assignee: Hitachi High-Technologies Corporation, Tokyo (JP)

( * ) Notice: Subject to any disclaimer, the term of this patent is extended or adjusted under 35 U.S.C. 154(b) by 259 days.

(21) Appl. No.: 12/352,357

(22) Filed: Jan. 12, 2009

(65) Prior Publication Data

US 2009/0121152 A1    May 14, 2009

Related U.S. Application Data

(62) Division of application No. 11/607,906, filed on Dec. 4, 2006, now Pat. No. 7,485,858.

(30) Foreign Application Priority Data

Dec. 6, 2005   (JP) .................................. 2005-352304

(51) Int. Cl.
    *G01N 23/00*        (2006.01)
    *G21K 7/00*         (2006.01)
    *A61N 5/00*         (2006.01)

(52) U.S. Cl. ....... 250/306; 250/307; 250/311; 250/492.2

(58) Field of Classification Search .................. 250/306, 250/307, 310, 311, 492.2; 382/145–149
See application file for complete search history.

(56) References Cited

U.S. PATENT DOCUMENTS

| | | | |
|---|---|---|---|
| 5,801,965 A | 9/1998 | Takagi et al. | |
| 6,039,000 A * | 3/2000 | Libby et al. | 250/310 |
| 6,259,960 B1 * | 7/2001 | Inokuchi | 250/310 |
| 6,438,438 B1 | 8/2002 | Takagi et al. | |
| 6,476,398 B1 * | 11/2002 | Xu et al. | 250/396 R |
| 6,546,308 B2 | 4/2003 | Takagi et al. | |
| 6,756,589 B1 | 6/2004 | Obara et al. | |
| 6,812,462 B1 * | 11/2004 | Toth et al. | 850/1 |
| 7,738,693 B2 * | 6/2010 | Luque | 382/145 |
| 7,834,315 B2 * | 11/2010 | Zaykova-Feldman et al. | 250/307 |
| 2001/0019411 A1 * | 9/2001 | Nara et al. | 250/310 |
| 2001/0020194 A1 | 9/2001 | Takagi et al. | |
| 2002/0145112 A1 * | 10/2002 | Davidson | 250/307 |
| 2003/0089852 A1 * | 5/2003 | Ochiai et al. | 250/310 |
| 2004/0158409 A1 * | 8/2004 | Teshima et al. | 702/22 |
| 2004/0188611 A1 * | 9/2004 | Takeuchi et al. | 250/310 |
| 2004/0260496 A1 * | 12/2004 | Ninomiya et al. | 702/84 |
| 2005/0024632 A1 | 2/2005 | Plemmons et al. | |
| 2006/0219914 A1 * | 10/2006 | Suga et al. | 250/311 |
| 2006/0289752 A1 * | 12/2006 | Fukunishi et al. | 250/310 |
| 2007/0053581 A1 * | 3/2007 | Ueno et al. | 382/149 |
| 2007/0127016 A1 | 6/2007 | Meeks et al. | |
| 2008/0296498 A1 * | 12/2008 | Hong | 250/311 |

FOREIGN PATENT DOCUMENTS

| | | |
|---|---|---|
| JP | 7-201946 A | 8/1995 |
| JP | 2000-30652 A | 1/2000 |
| WO | WO 00/03413 A1 | 1/2000 |

\* cited by examiner

*Primary Examiner* — Robert Kim
*Assistant Examiner* — Brooke Purinton
(74) *Attorney, Agent, or Firm* — McDermott Will & Emery LLP

(57) ABSTRACT

An object of the present invention is to provide a suitable method of observing a wafer edge by using an electron microscope. The electron microscope includes a column which can take an image in being tilted, and thus allows a wafer edge to be observed from an oblique direction.

3 Claims, 9 Drawing Sheets

FIG. 11 A
FIG. 11 B
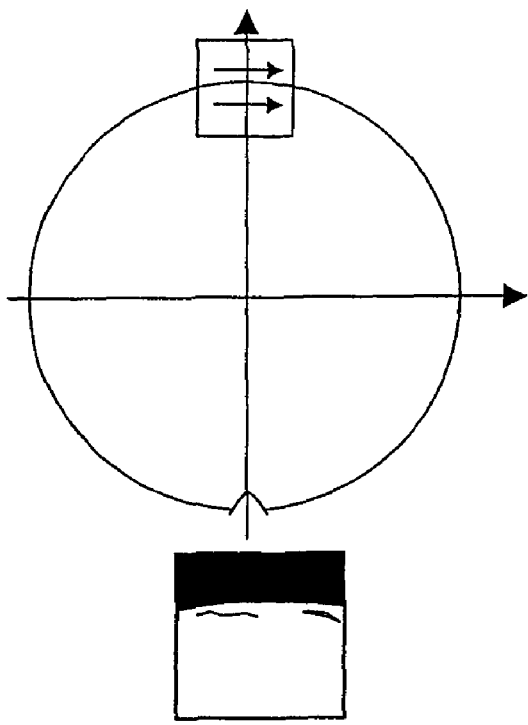
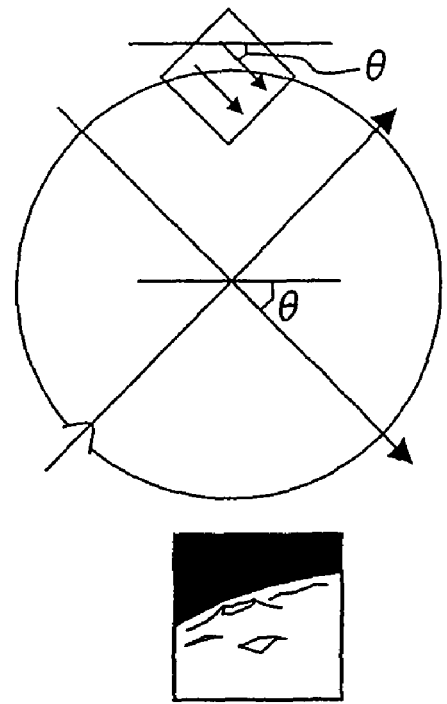

INSPECTION METHOD FOR SEMICONDUCTOR WAFER AND APPARATUS FOR REVIEWING DEFECTS

RELATED APPLICATIONS

This application is a Divisional of U.S. application Ser. No. 11/607,906, filed Dec. 4, 2006, now issued as U.S. Pat. No. 7,485,858 on Feb. 3, 2009, claiming priority of Japanese Application No. 2005-352304, filed Dec. 6, 2005, the entire contents of each of which are hereby incorporated by reference.

BACKGROUND OF THE INVENTION

1. Field of the Invention

The present invention relates to a method and an apparatus for reviewing defects that have occurred in processes of manufacturing thin film devices such as semiconductor electronic circuit substrates and liquid crystal display substrates, by using a magnification image-pickup apparatus such as a scanning electron microscope.

2. Description of the Related Art

Manufacturing of thin film devices, such as semiconductors, liquid crystal displays, and magnetic heads for hard disks, includes a large number of processes. The number of such manufacturing processes sometimes sums to several hundreds. In a case where defects such as particles and breaks in wiring occur in thin film devices due to unsatisfactory or malfunctioned manufacturing conditions in processing apparatuses, this results in an increase of the probability at which defects occur in products, and consequently, a decrease in a yield. With this taken into consideration, it is important that an apparatus in which a problem occur be identified, and that countermeasures be taken for the purpose of maintaining and improving the yield. To this end, a particle inspection, a pattern inspection and the like are performed for every main process, and thereby it is monitored whether processing is normally performed. At this time, it is not possible to perform inspections on all the substrates to-be-processed due to restrictions on time and labor. For this reason, generally, inspections are performed on substrates to-be-processed sampled on a lot basis or on a substrate to-be-processed basis, for each series of several processes. Here, a substrate to-be-processed denotes a minimum unit being processed. In a case of a semiconductor, a substrate is one sheet of wafer.

In a case where a particle inspection is performed by using an inspection apparatus, for example, a wafer surface is scanned by a laser, and thereby a detection is made as to whether there is scattered light. Thus, information on the positions and the number of particles is obtained. In addition, in a case where a defect inspection is performed on particles and pattern defects together, an image of a circuit pattern of a wafer is captured with, for example, an optical magnification image pickup device, and information on the positions, the number and the like of defect points is obtained, by comparing images in adjacent areas in the same pattern with one another. Here, a "defect point" denotes a point, which is outputted as a point at which an abnormality is found out by an inspection by using an inspection apparatus. Hereinafter, the inclusion of particles and pattern defects are referred to as "defects."

A determination as to a device malfunction is often made by using, as a control index, the number and the density of defects detected by an inspection apparatus. That is, it is determined that a device malfunction has occurred when the number of defects exceeds a predetermined reference value. On the basis of defect coordinate information detected by the inspection apparatus, images of the defects are magnified, and the images thus magnified are taken by using a review apparatus such as an optical microscope or a scanning electron microscope (SEM). Thus, detail information on the sizes, shapes, textures and the like of the defects is obtained by taking images of magnified defects. In addition, detail inspections, such as an elemental analysis and a cross-sectional observation and the like, are performed, and thereby it is identified which of the apparatuses is malfunctioning and which mode of defect occurs. By using these results, measures are taken for apparatuses and processes, thereby preventing a yield from decreasing.

In order to automate such review operations and make them more efficient, review apparatuses having a function (Automatic Defect Review: ADR) have been recently developed (refer to Japanese Patent Application No. 2000-30652). The ADR function causes magnified images of particles and defects to be automatically captured by using inspection data from a particle inspection apparatus and a defect inspection apparatus. Moreover, Japanese Patent Application No. Hei 7 (1995)-201946 discloses a technique in which captured images are automatically classified (Automatic Defect Classification; abbreviated as ADC) according to a specific rule.

SUMMARY OF THE INVENTION

In manufacturing processes of semiconductors, a process such as forming, processing and washing a thin film is repeated many times. During the manufacturing processes, there is a case where the adhesion of a formed film is deteriorated in an outermost periphery of a wafer due to some factors such as the adhesion of particles and surface roughness. In this case, sometimes, not only the poor adhesive film tends to be easily peeled off in the process of forming the poor adhesive film, but also films tend to be easily peeled off from the outermost periphery in subsequent processes. The films thus peeled off are adhered as particles to a processed circuit pattern, causing an electrical defect in some cases. For this reason, after forming films, a wafer edge is sometimes observed to check whether or not there is a problem in the formation state of the films such as roughness and peeling. Since the width and interval of recent wiring are on the order of submicrometers, the sizes of particles and defects to be observed are also on the same order. As means for performing a detail observation on such micro particles and defects, electron microscopes are mainly used.

While a usual defect is generally observed from a vertically upper position of a wafer, it is preferable that a defect be observed not from a vertically upper position but from an obliquely upper position so that a side surface is easily observed, in order to perform a detail observation on a wafer edge. Such a technique for observing wafer edges is described, for example, in Japanese Patent Application No. 2001-221749. However, the above-describe document does not disclose a preferable technique using an electron microscope as an observation apparatus.

An object of the present invention is to provide a suitable method for observing a wafer by using an electron microscope.

A semiconductor wafer inspection method is characterized by including the steps of: placing a semiconductor wafer on a sample stage of an electron beam apparatus having a first electron beam optical system for irradiating an electron beam from a direction normal to a surface of a sample, and a second electron beam optical system for irradiating an electron beam from a direction tilted from the direction normal to the surface; obtaining defect position data on the semiconductor wafer from an inspection apparatus; moving the stage to a position corresponding to a defect position obtained from the inspection data, and capturing a scanned image of a defect by using the first electron beam optical system; discriminating a mode of the defect on the basis of the captured defect image; determining whether there is a defect which has been discriminated as one of a peeling mode; and capturing a scanned image of an edge portion of the semiconductor wafer by using the second electron beam optical system, when it is determined in the above determination that there is a defect of the peeling mode.

An area to be imaged by the second electron beam optical system is determined in an edge portion of the semiconductor wafer according to a distribution of defects of the peeling mode on the semiconductor wafer. It is preferable that a scanning direction of an electron beam by the second electron beam optical system be controlled in proportion to a rotation angle of the stage so that the scanning direction would be tilted at the same angle as the rotation angle of the sample stage.

A defect review apparatus of the present invention includes a sample stage, a first electron beam optical system, a second electron beam optical system, a display unit, and later described means. The sample stage moves with a semiconductor wafer held. The first electron beam optical system irradiates an electron beam from a direction normal to a surface of the semiconductor wafer held on the sample stage. The second electron beam optical system irradiates an electron beam from a direction tilted from the direction normal to the surface. The display unit displays an image of the surface of the semiconductor wafer, and the image is generated by the irradiation of the electron beam. As for the means, the following functions are carried out. Firstly, defects are classified according to an image of the defects captured by using the first electron beam optical system. Secondly, the display unit is caused to display a wafer map showing the positions of the defects of a peeling mode on the semiconductor wafer in a manner discriminating the defects of the peeling mode from the defects of the other modes. Thirdly, a scanned image of an edge of the semiconductor wafer is captured by using the second electron beam optical system, and then display unit is cause to display the scanned image.

When the sample stage is rotated, a scanning direction of an electron beam by the second electron beam optical system may preferably be tilted at the same angle as the rotation angle of the sample stage.

According to the present invention, it is possible to effectively observe a wafer edge in a semiconductor wafer review by using an electron microscope.

BRIEF DESCRIPTION OF THE DRAWINGS

FIG. 11 is a view showing an example of an image pickup method of the present invention.

DETAILED DESCRIPTION OF THE PREFERRED EMBODIMENTS

An embodiment of the present invention is described below by referring to the accompanying drawings.

Figure 1:
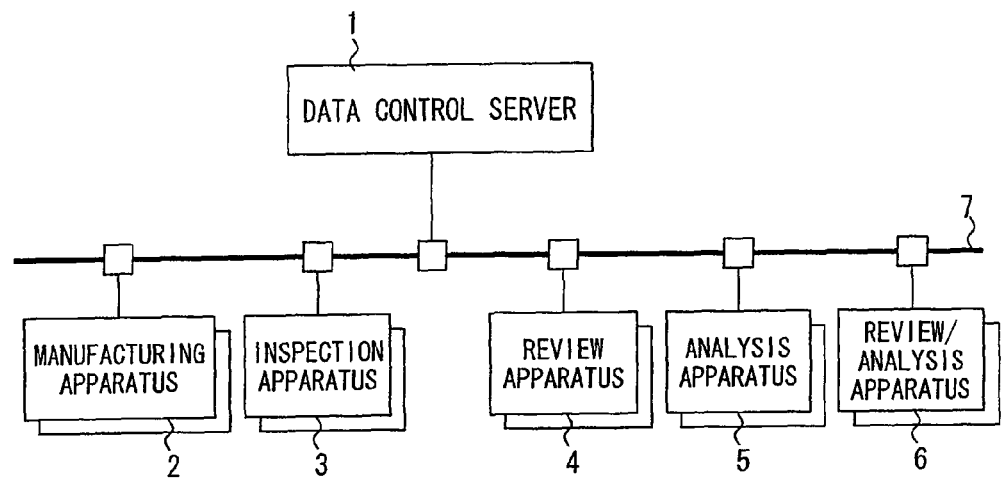
FIG. 1 is a view for showing an example of a connection configuration of apparatuses on a manufacturing line for wafers.

By using FIG. 1, descriptions will be given, as a specific example, of each of apparatuses on a wafer manufacturing line and a connection configuration thereof. In FIG. 1, reference numeral 1 denotes a data control server; reference numeral 2, a semiconductor manufacturing apparatus; reference numeral 3, an inspection apparatus; reference numeral 4, a review apparatus; reference numeral 5, an analysis apparatus; reference numeral 6, a review/analysis apparatus; and reference numeral 7, a network. As shown in FIG. 1, the manufacturing line has a configuration in which the semiconductor wafer manufacturing apparatus 2, the inspection apparatus 3, the review apparatus 4, the analysis apparatus 5 and the review/analysis apparatus 6 are connected to one another via the data control server 1 and the network 7.

The manufacturing apparatus 2 has a function as a lithography machine, an etching system and the like, and is used for manufacturing of a semiconductor wafer. The inspection apparatus 3 inspects the positions of defects. For example, the inspection apparatus 3 causes a light beam spot or a light beam line to scan a semiconductor wafer and, thereby, identifies the positions of defects on the basis of the degree of its diffuse reflection. Alternatively, the inspection apparatus 3 obtains images of formed patterns of two chips, compares these images with each other, defines, as defects, portions whose images are different, and thus detects the positions of the defects. The review apparatus 4 observes the defects by using inspection information of the inspection apparatus 3. The review apparatus 4 moves a stage on which a semiconductor wafer is mounted, positions the stage for target defects on the semiconductor wafer by using defect position information outputted from the inspection apparatus 3, and thereby, observes the defects. As an observation apparatus, an SEM is used. The analysis apparatus 5 performs an elemental analysis by using, for example, energy-dispersive X-ray spectroscopy (EDX) and Auger electron spectroscopy. Auger electron spectroscopy is a generally-known method in which, when an electron beam is irradiated to a target, Auger electrons emitted from the target are detected and analyzed. The review/analysis apparatus 6 is capable of observing defects and performing an elemental analysis on the defects.

Incidentally, the apparatus for inspection, observation and analysis are not necessarily separated from one another. These functions may be combined with one another to form one apparatus. For example, an inspection and a review may be performed in the same apparatus.

The data control server 1 controls data obtained by the inspection apparatus 3, the review apparatus 4, the analysis apparatus 5, and the review/analysis apparatus 6. The review apparatus 4 and the analysis apparatus 5 can obtain information on defect position coordinates outputted from the inspection apparatus 3 through data control server 1, and the like. Specifically, the review apparatus 4, the analysis apparatus 5 or the review/analysis apparatus 6 obtains defect position coordinate data obtained in the inspection apparatus 3, positions the stage to target defects by using the coordinate data, the apparatus 4, 5 or 6, and performs a review and an analysis.

In the above, though one example of the connection configuration is described, any connection configuration can be employed as long as data can be sent and received between the apparatuses, thus being used in the apparatuses. In addition, all the apparatuses in the present configuration are not necessary, and any combination thereof may be made according to an object.

Figure 2:
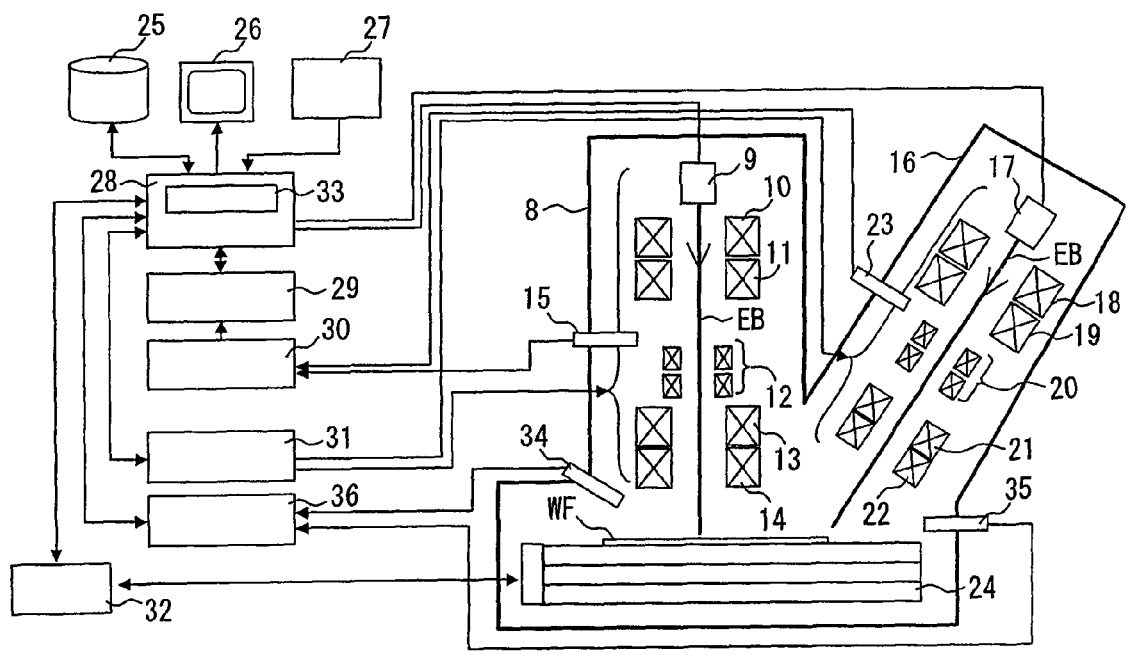
FIG. 2 is a view showing an example of an apparatus configuration of the present invention.

FIG. 2 is a view showing one example of an apparatus configuration. Reference characters WF denotes a semiconductor wafer; reference characters EB, an electron beam; and reference numeral 8, a first image-pickup device using a scanning electron microscope. This is referred to as a first column. Reference numeral 9 denotes an electron source; reference numerals 10 and 11 condenser lenses of the first column; reference numeral 12, a deflection scan coil of the first column; reference numerals 13 and 14, objective lenses of the first column; and reference numeral 15, a detector of the first column. Reference numeral 16 denotes a second column; reference numeral 17, an electron source of the second column; reference numerals 18 and 19, condenser lenses of the second column; reference numeral 20, a deflection scan coil of the second column; reference numerals 21 and 22, objective lenses of the first column; and reference numeral 23, a detector of the second column. Reference numeral 24 denotes an XYθ stage; reference numeral 25, a storing device; reference numeral 26, a monitor; reference numeral 27, an input device; reference numeral 28, an entire control unit; reference numeral 29, an image calculation unit; reference numeral 30, an A/D converter; reference numeral 31, an electron optical system control unit; 32 a stage control unit; and 33 a defect data analysis calculation unit. Reference numerals 34 and 35 denote detectors for element analysis, and 36 an element analysis control unit. In FIG. 2, the first column 8 includes the electron source 9, the electron optical systems 10 to 14, and the detector 15, while the second column 16 includes the electron source 17, the electron optical systems 18 to 22, and the detector 23. The first column 8, the second column 16, and the XYθ stage 24 form an SEM, which is used as an image pickup apparatus for a semiconductor wafer WF mounted on the XYθ stage 24.

The semiconductor wafer, which is a target for a review, is mounted on the XYθ stage 24. The stage control unit 32 controls the movement of the XYθ stage 24 in the directions X and Y, and the rotation θ according to a control signal from the entire control unit 28. The first column 8 magnifies an image of the semiconductor wafer WF fixed to the XYθ stage 24, and takes the magnified image. To be more precise, an electron beam EB emitted from the electron source 9 is converged by the condenser lenses 10 and 11, and the objective lenses 13 and 14, and then is scanned by the deflection scan coil 12. Thus, the electron beam EB is irradiated to the semiconductor wafer WF, which is a measuring target. With this irradiation, secondary electrons and reflection electrons are obtained from the semiconductor wafer WF. Then, the secondary electrons and reflection electrons are detected by the detector 15, and are processed by the A/D converter 30, thus generating an SEM image of the semiconductor wafer WF.

In the same manner, the second column 16 magnifies an image of the semiconductor wafer WF fixed to the XYθ stage 24, and takes the magnified image. That is, an electron beam emitted from the electron source 17 is converged by the condenser lenses 18 and 19, and the objective lenses 21 and 22, and then is scanned by the deflection scan coil 20. Thus, the electron beam EB is irradiated to the semiconductor wafer WF, which is a measuring target. With this irradiation, secondary electrons and reflection electrons are obtained from the semiconductor wafer WF. The secondary electrons and reflection electrons are detected by the detector 23, and are processed by the A/D converter 30, thus generating an SEM image of the semiconductor wafer WF.

The first column 8 and the second column 16 are placed so that the angles of the axes of electron optical systems thereof are different. For example, while the axis of the electron optical system of the first column 8 is parallel to the direction of the normal to a surface of a wafer, the second column 16 is placed so that the axis of the electron optical axis thereof is tilted at some angle to the direction of the normal thereto. Thus, it is possible to obtain information by performing observations from different angles by using the first column 8 and the second column 16.

In a case where, for example, an EDX analysis is used as the elemental analysis method, the detectors 34, 35 detect X-rays generated after irradiating an electron beam on a measuring target. The element analysis control unit 36 receives a control signal from the entire control unit 28, and controls ON/OFF of X-ray detection. The element analysis control unit 36 or the entire control unit 28 performs a spectral analysis on the thus detected X-ray spectra. As a result of the analysis, information on contained elements is extracted, and then is displayed to a user on the display device 26.

Figure 3:
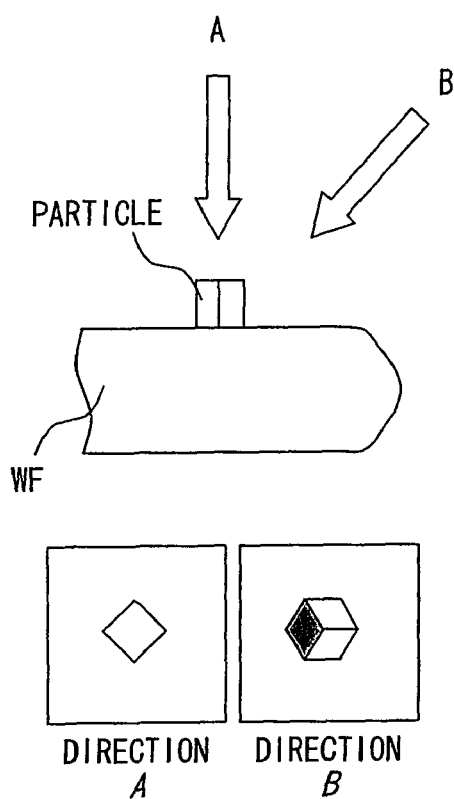
FIGS. 3A and 3B are views describing a difference between captured images due to a difference between observation angles.
Figure 3:
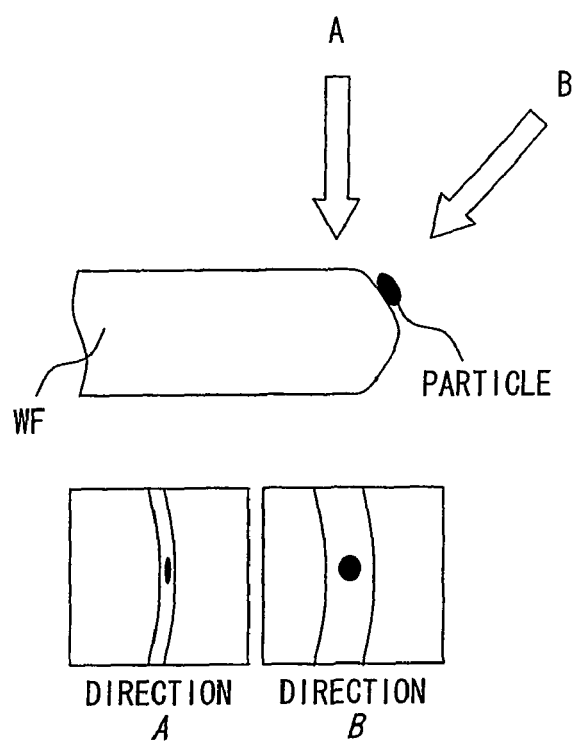

FIGS. 3A and 3B shows an example of directions in which a wafer is observed. FIGS. 3A and 3B are views showing the wafer viewed from the vertical sectional direction. For example, the first column is disposed so that a wafer is imaged from the direction A, and the second column is disposed so that a wafer is imaged in the direction B. In the case where the columns are disposed as described above, FIG. 3A shows examples of observation images obtained when a particle of a rectangular shape is imaged, and FIG. 3B shows examples of observation images obtained when a wafer edge is imaged.

In a case where the particle is imaged as shown in FIG. 3A, side surfaces of the particle can be observed from the direction B. In a case where the wafer edge is imaged as shown in FIG. 3(b), it is not easy to obtain the information on the shape and the like of the particle adhering to the wafer edge when viewed from the direction A. In contrast, it is easier to obtain the information on the shape and the like of the particle when viewed from the direction B, since the edge can be observed from a more front side than viewed from the direction A.

Which column is used for imaging is instructed by a user through the input device 27, or is controlled by the entire control unit 28 using a result of a calculation performed by the entire control unit 28 according to a predetermined rule. On the basis of a control signal, the stage control unit 32 controls the stage position corresponding to a column to be used. The electron optical system control unit 31 transmits a control signal of the electron optical system to the column. Then, the A/D converter 30 captures an image from the column.

The defect data analysis calculation unit 33 performs image processing such as defect detection processing. A user inputs input items such as defect observation conditions from the input device 27. Defect coordinate data for reviewing is transmitted from the inspection apparatus to the entire control unit 28 through an unillustrated network. The stage control unit 32 performs a control based on detect coordinate data so that a defect comes in sight. In the case of this embodiment, only one detector is illustrated as each of the detectors 15 and 23, but a plurality of detectors may be disposed according to an application in which, for example, detections are performed by dividing a range for the energy of electrons to be detected.

Figure 4:
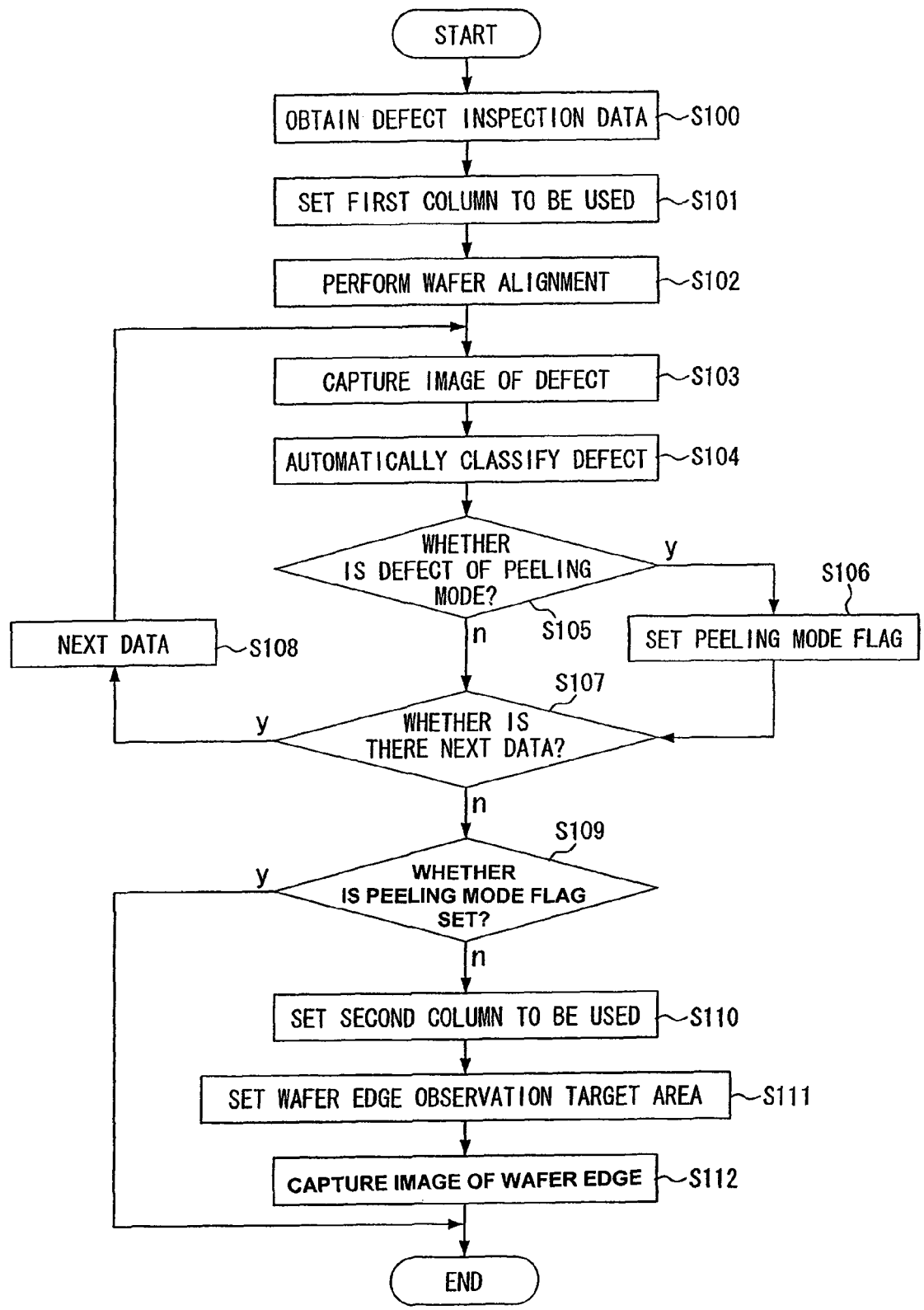
FIG. 4 is a flowchart showing an example of an observation process using the apparatus of the present invention.

Next, FIG. 4 is a flowchart of a first example of an observation method in which the first column and the second column are used by switching when a wafer is observed. First, in step S100, defect inspection data outputted from the defect inspection apparatus 3 are read. Subsequently, in step S101, as a column to be used, a usual defect observation column is set to be used. For example, the first column, whose axis of the electron optical system is parallel to the normal to a wafer, is set to be used. The, in step S102, an alignment of a wafer is performed. This is a step in which a coordinate difference between an observation apparatus and an inspection apparatus is corrected. For example, an alignment mark is observed by the observation apparatus, and the position of the alignment mark is manually specified or automatically recognized. Then, the coordinates of the thus found position are compared with the outputted coordinates of the alignment mark in the inspection apparatus, so that a translational dislocation and differences in contraction scale and rotation are corrected.

Next, in step S103, the images of defects are automatically captured on the basis of defect inspection data. In step S104, the thus captured images are automatically classified according to a predetermined rule. At this time, as an unillustrated previous arrangement, it is necessary to make a rule for classification and data on instruction to classify as well, which allow particles/defects resulting from film peeling on a wafer to be classified. In step S105, it is determined whether or not a defect classification result indicates that a defect is a particle/defect resulting from film peeling on a wafer, i.e., whether or not the defect belongs to a peeling mode. A particle/defect resulting from film peeling on a wafer often has a shape of a small torn piece of a thin film-like substance. For this reason, it is very likely that such a defect can be discriminated by checking the appearance features. If information on classifications in which the particles/defects have similar appearance features, for example, the shapes and luminance of defects is collected, in advance, from images of the particles/defects on a process basis, highly reliable discriminations can be achieved. If a defect belongs to the peeling mode, a peeling mode flag is set in step S106 so that the presence of the defect of the peeling mode can be stored. If it is determined that the defect does not belongs to the peeling mode, the process goes to step S107 without performing step S106.

In step S107, it is determined whether or not there is the next defect to be observed. If there is a defect, data are read in step S108 and, thereafter, steps starting from step S103 are repeated in the same manner. If it is determined in step S107 that there is no next defect to be observed, it is determined in step S109 whether or not there is a defect of the peeling mode in defects to be observed. That is, it is determined whether or not a peeling mode flag is set. If the peeling mode flag is not set, the defect observation on the inspection data is terminated.

If the peeling mode flag is set, the second column is set to be used as an observation column, in step S110. In step S111, a target area for observing a wafer edge is set. This may be set in advance in a recipe in which a procedure of observing defects is recorded, may be automatically set according to an analysis result of captured defect images, as is described later, or may be manually set by a user. As setting contents of the observation target area, for example, the entire circumference of a wafer may be set, or a coordinate range may be set. The coordinates may be expressed by using an X-Y coordinate system or a polar coordinate system. Alternatively, an outline of a wafer may be graphically displayed, and thus a user may designate which area to be used as an observation target by using the outline drawing. Subsequently, in step S112, an image in a wafer edge area thus designated is captured, and thereafter the process is terminated.

Descriptions are given of an example of a method for setting automatically a target area for observing a wafer edge according to an analysis result of captured defect images.

Figure 5:
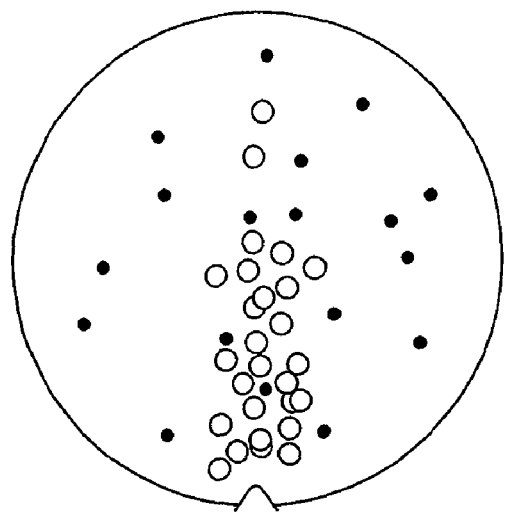
FIGS. 5A and 5B are views each showing an example to explain a wafer edge observation position determination method of the present invention.
Figure 5:
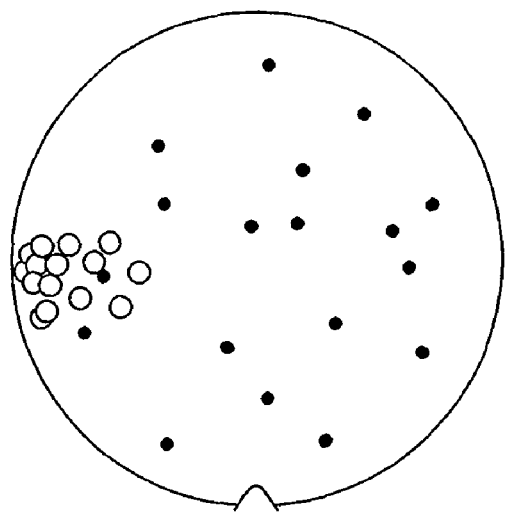

A map showing the positions of defects in a wafer is, hereinafter, referred to as a wafer map. FIGS. 5A and 5B are views showing examples of wafer maps of wafers to be observed. In FIGS. 5A and 5B, a coordinate point of a defect which is classified into the peeling mode is represented as a white circle. Focusing only on defects of the peeling mode, it is understood in FIG. 5A that the defects are distributed only in the vertical direction and that many of them exist on the side of a V-notch. In this case, it is estimated that a film is peeled off in an edge on the side of the V-notch due to some factor, and that particles are formed because of the film peeling, and spread in the vertical direction. In this case, an edge on the side of the V-notch may be set as an observation target area. On the other hand, in FIG. 5B, defects of the peeling mode are concentrated in a narrow area of a wafer edge. In this case, the periphery of the edge in which defects occur in concentration may be set as an observation target area.

Figure 6:
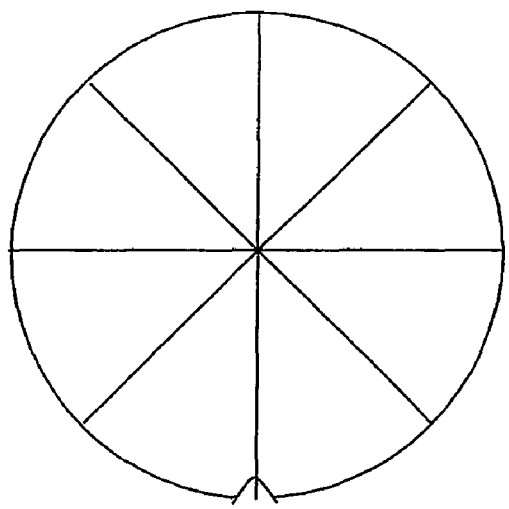
FIG. 6 is a view showing an example to explain the wafer edge observation position determination method of the present invention.

In order to make determinations such as above, as shown in FIG. 6, for example, a wafer is divided into several radial regions, and a value showing a frequency of the presence of a defect of the peeling mode in each region, e.g., the number or the density thereof, is calculated. A wafer edge of a region, the value of which is high, may be set as an observation target area.

A method in which an observation target is obliquely observed is not limited to the above. For example, a structure may be employed, in which only the first column is disposed in a tilting manner. Alternatively, a structure may also be employed, being capable of varying a tilt angle at which the column is disposed. In a case of the structure in which the tilt angle is variable, step S110 in the flowchart shown in FIG. 4 is replaced with a step in which the tilt angle of the column is changed. Otherwise, by tilting the stage, an observation from an oblique direction may be performed. In this structure, step S110 in the flowchart of FIG. 4 is replaced with a step in which the tilt angle of the stage is changed. An electron beam for irradiation may be deflected and, thereby, images observed from an oblique direction may be captured by obliquely irradiating the electron beam thus deflected. In this structure, step S110 in the flowchart of FIG. 4 is replaced with a step in which the direction of a beam irradiation is changed.

Next, descriptions are given of another example of a setting method in an observation target area of a wafer edge. The following may be an example of the flowchart in FIG. 4 or an example in the case only a wafer edge is set as an observation target.

In a first example of a setting method of an observation target area in a wafer edge, by using inspection data from an inspection apparatus for wafer edge inspection, an observation target area may be set with the outputted coordinates of the inspection data set as the center of a viewing field. The size of a viewing field may be set as a fixed value by a user or may be automatically changed on the basis of the size of defects.

Figure 7:
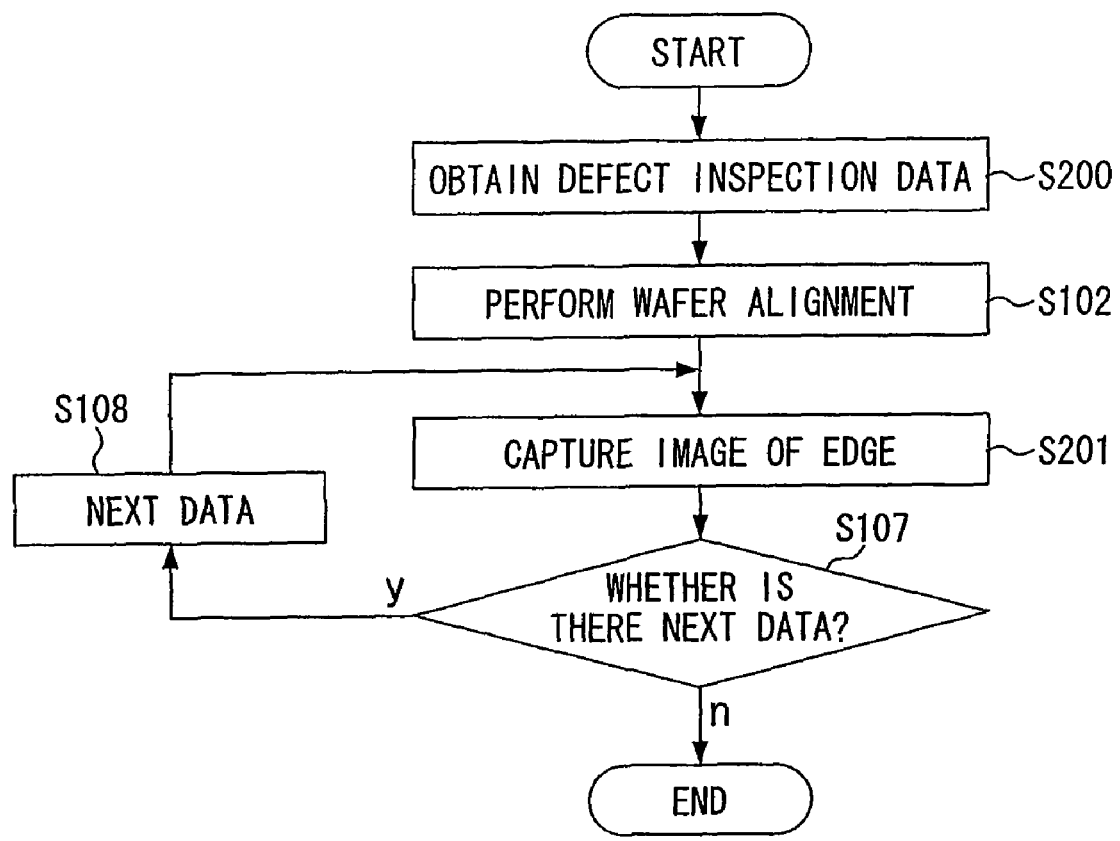
FIG. 7 is a flowchart showing an example of an observation process using the apparatus of the present invention.

FIG. 7 is an example of an observation flow in a case where only a wafer edge is to be observed by using the above setting method. The same reference numerals are given to steps that are the same as those in FIG. 4. First, in step S200, data from an inspection apparatus for wafer edge inspection is obtained.

Subsequently, in step S102, a wafer alignment is performed. Next, a viewing field is moved according to the inspection data thus read, and an edge image is captured in step S201. The image is an image indicated by the coordinates outputted from the inspection apparatus as a position at which a defect exits, and is expected to be an image containing the defect. Thereafter, Steps S107 and S108 are performed, and then the process is terminated.

In a second example, a user may designate an observation position and its area in advance. As the designated position, for example, a user may regularly set positions at a certain fixed intervals, or may set a particular position such as a periphery of a V-notch or a chuck position of a processing apparatus. In a third embodiment, the entire periphery of a wafer may be set as an observation target.

Figure 8:
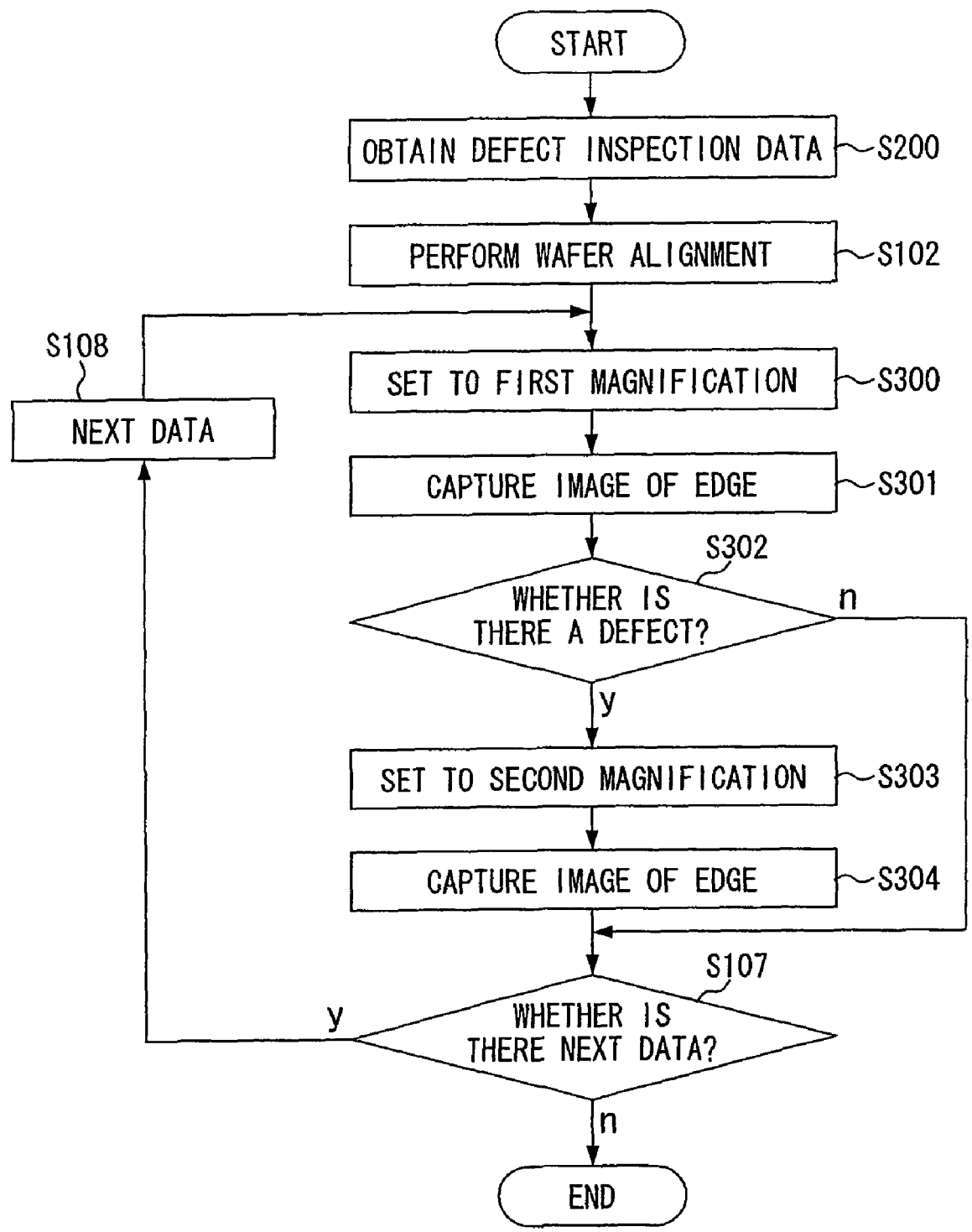
FIG. 8 is a flowchart showing an example of an observation process using the apparatus of the present invention.

When an image of a wafer edge is captured, a wafer edge may be firstly imaged at a certain first magnification. Then, only when a defect is found in an image captured at the first magnification, the wafer edge may be imaged at a second magnification higher than the first magnification with the position of the defect set as the center of a viewing field. An example of an imaging flow in the above case is shown in FIG. 8. Steps S200 and S102 are performed as in the case of the example in FIG. 7, and the first magnification is set in step S300. In consideration of coordinate output errors of an inspection apparatus and positioning errors of an observation apparatus, it is preferable that the first magnification be set to be the one at which a defect is included in the area of a viewing field even when the errors occur. Next, in step S301, an edge image is captured at the first magnification. Then, in step S302, a determination is made as to the presence or absence of a defect, and the position of the defect is specified when the defect exists. If it is determined that the defect exists, the magnification is set to the second one in step S303. The second magnification may be designated in advance by a user. Alternatively, in a case where defect size information is contained in inspection data from the inspection apparatus, the second magnification may be variable according to the information. Otherwise, the size of a defect is calculated in advance in a defect presence/absence determination process of step S302, and the second magnification may be variable according to the thus calculated value.

In general, the second magnification is set to be higher than the first magnification so that a more detailed observation on a defect part can be performed. However, in a case where it is determined in a determination process of step S302 that a area in which defects exit is larger than the area of a viewing field at the first magnification, a magnification lower than the first magnification may be set. In step S304, an edge image is captured at the second magnification. Next, Steps S107 and S108 are performed and, thereafter, the process is terminated. In a case where it is determined in step S302 that there is no defect, the process goes to step S107.

As a method for determining the presence/absence of a defect and for detecting the position thereof, there are the following methods, for example. In one of the methods, an Image showing a normal state is registered in advance, and compared with images captured at the time of observation of a wafer edge. Thereby, a portion having a large difference is determined as a defect. In another one of the methods, a viewing field is divided into a plurality of small regions, and the luminance dispersion of picture elements composing an image is calculated for each small region. When the dispersion exceeds a predetermined threshold, it is determined that the surface of the small region is rougher than is an expected normal portion, and consequently determined that the small region has a defect. At this time, when a wafer edge and a background are contained in the small region, the dispersion becomes so large that the small region is likely to be erroneously determined as a defect region. In this case, such a region may be eliminated from defect candidates. Alternatively, in this case, picture elements with the viewing field lower than certain viewing field are determined as those of a background by using a difference of the viewing field of picture elements, so that the picture elements of the lower viewing field are not used for calculation of the dispersion. In still another one of the methods, a differential value indicating the magnitude of a change in the viewing field of images is calculated, and thereafter a region at which the differential value is large is determined as a defect region by excluding a boundary region of a wafer edge. Yet another one of the methods uses a phenomenon that secondary electrons generated when an electron beam is irradiated generally increase at an uneven portion of a target, that is, that the luminance of an image at the uneven portion becomes higher. Thus, the region of the highest luminance is determined as a defect region. At this time, since there is a possibility that luminance abruptly becomes high due to a noise, it is preferable to perform a preprocess for every small region. Examples of the preprocess include a process of averaging and a process using a low-pass filter.

The number of methods to be selected from the above methods is not necessary one, and a plurality of methods may used. In addition, a user may select at least one method.

In a case where, when performing the defect determinations such as above, a defect is found or the frequency of defects exceeds a predetermined threshold, a warning may be issued to let a user know that a wafer edge is abnormal. Such a warning may be displayed on the monitor 26 of an electron microscope, or on another display device connected to another network through the network 7. Otherwise, an e-mail may be sent as such a warning to a person in charge through a mail system not shown.

When a wafer edge is observed, not only images but also element analysis information such as EDX may be obtained.

Figure 9:
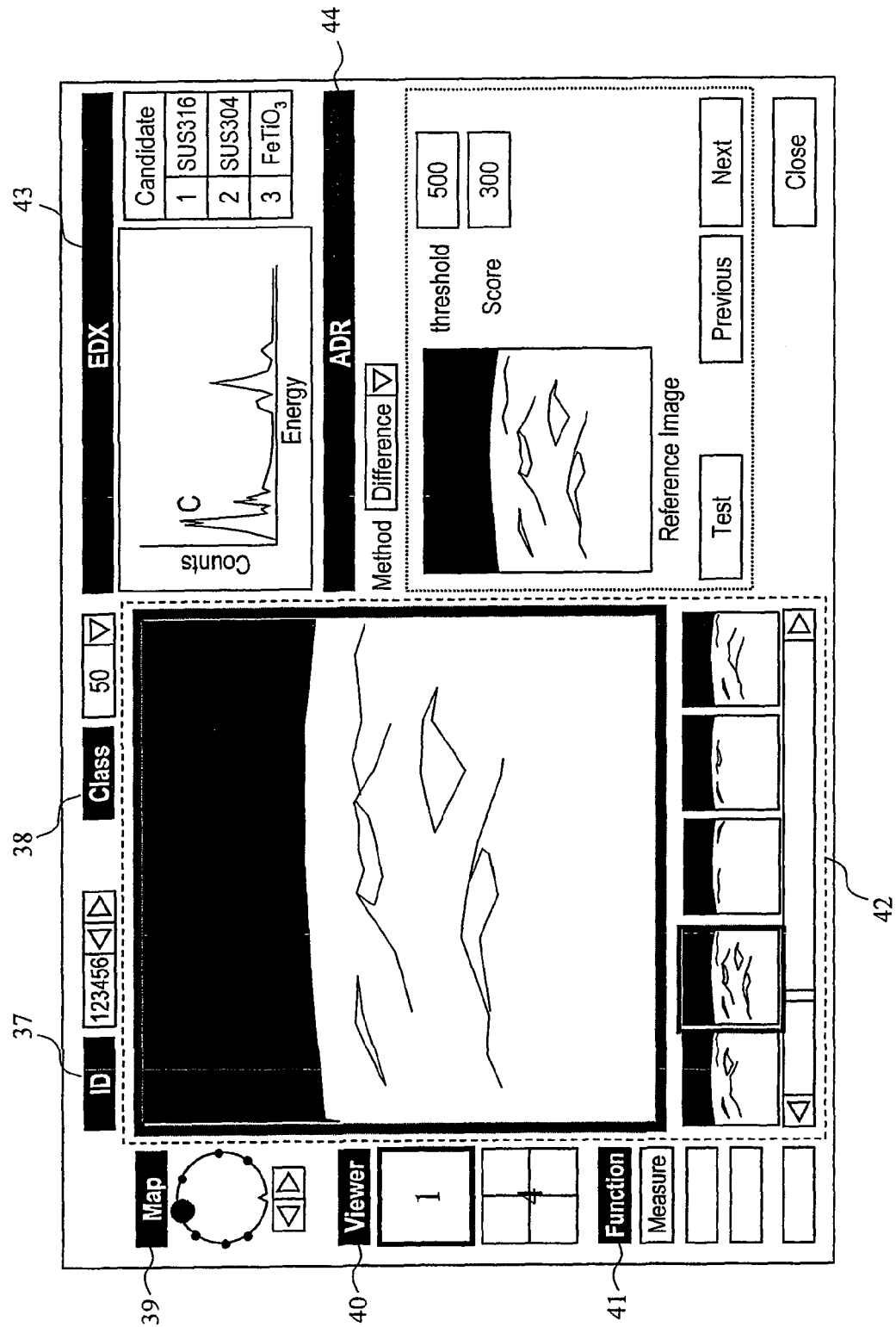
FIG. 9 is a view showing an example of a screen display of the present invention.
Figure 10:
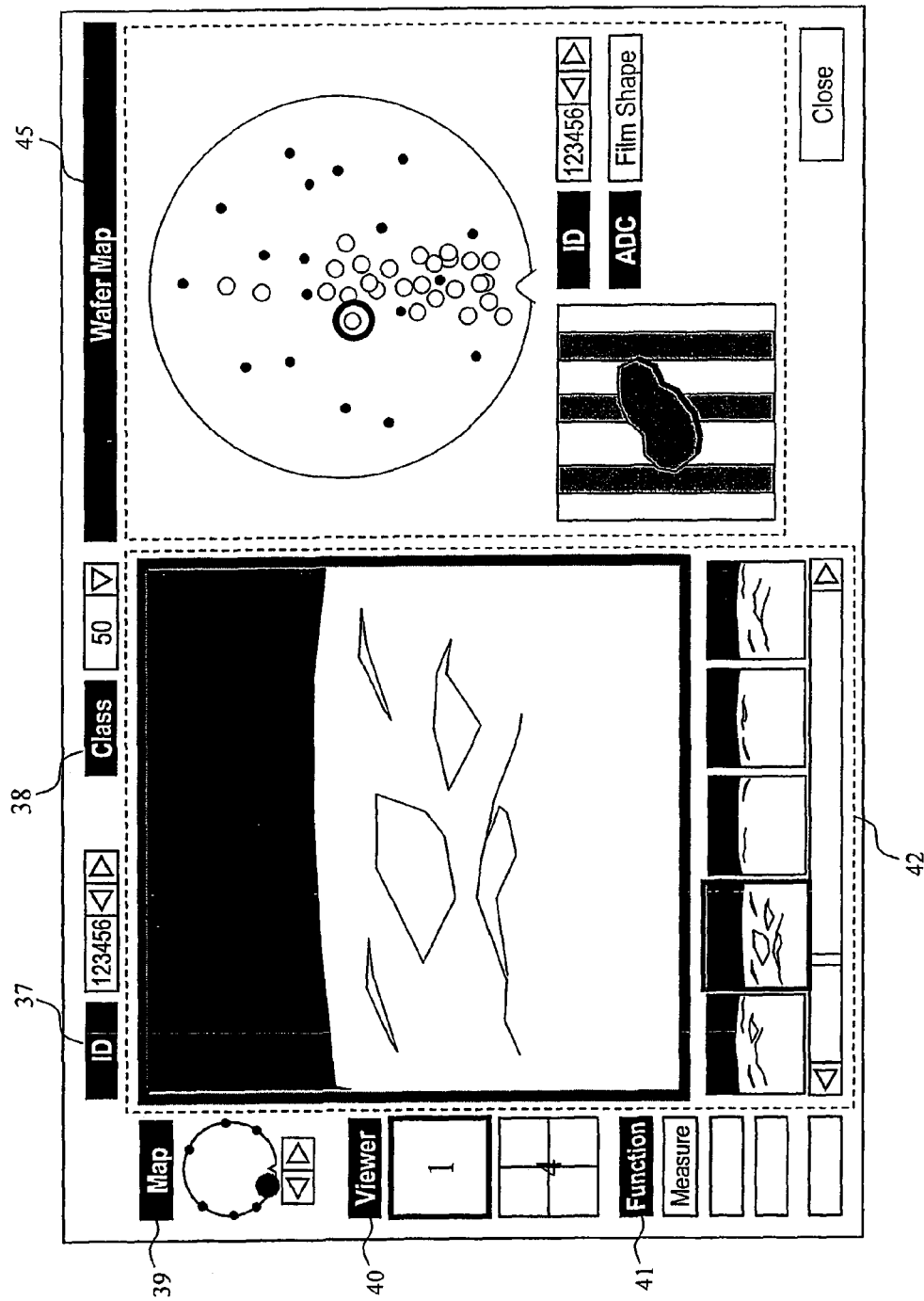
FIG. 10 is a view showing an example of the screen display of the present invention.

FIGS. 9 and 10 are views each showing an example of a GUI in which operational functions for an edge review and captured images are displayed. In FIG. 9, reference numeral 37 denotes a unique identifier of a defect added in an inspection apparatus or an observation apparatus. Reference numeral 38 denotes a classification identifier in a case of the automatic classification. Reference numeral 39 denotes a map display showing a position of a wafer edge in which a captured image is located. In the map display, a large circle represents the contour of a wafer, each of small filled circles represents a position at which an image is captured, and a large filled circle represents a position of an image displayed in an image display area located to the right-hand side of the map display. Each of arrow buttons below the map is a switch for changing the image to be displayed to a subsequent or previous one. In a case where the entire periphery of a wafer is a review target, an amount of movement may be automatically adjusted, as a function for an operation, according to an image magnification with one of the buttons pressed, so that a viewing field may be moved without having discontinuity between the areas of viewing fields.

Reference numeral 40 denotes a display used for designating a format of an image display among a format in which one image is displayed on the display area and a format in which a plurality of images are displayed by dividing the display area. Reference numeral 41 denotes a display used for selecting a function to be performed on a display image. For example, when Measure is selected, two line-shaped cursors are displayed overlapping the display image, and a user can move the cursors. Then, a dimension between the cursors is displayed in actual dimension in relation to an image magnification of an image. Reference numeral 42 denotes an image display area, in which an image under observation or a captured image is displayed. A display format is designated by use of reference numeral 40. In addition, a list including other zoomed-out images is displayed in the display area, a selected image may be displayed on the display area. A display magnification of the zoomed-out image may be changed, or the entire image may be scrolled, and thus be displayed. In relation to a selected image in the list area showing zoomed-out images, the size of a filled circle corresponding to the selected display image is enlarged so that a user can know a position where the image being displayed is imaged on the map display 39.

Reference numeral 43 denotes a display showing an element analysis result. This shows, for example, a waveform of an element analysis result, the symbols of detected elements, and the name and symbol of elements of a substance estimated from the waveform. Reference numeral 44 denotes a display used for causing an automatic detection process to be performed on a defect, and showing a condition and a result of a process. Parameters for a defect detection process are adjusted on the basis of the process result. Thus, by using the adjusted parameters, process parameters in a defect detection operation of an observation apparatus can be updated.

The display screen shown in FIG. 9 is just an example, and the display screen may display only part of display items shown in FIG. 9. In addition, displayed contents are not necessarily the same as those as above, but may be similar thereto. As shown in a display 45 of FIG. 10, a wafer map of detect inspection data on a wafer may be displayed along with a defect observation image which a first column takes corresponding to the inspection data. The display area 45 shows at least an image, an ID number and a classification result of a selected defect on the wafer map.

FIGS. 11A and 11B are views each showing an example in which a scanning direction is changed according to an observation position of a wafer when an image of a wafer edge is captured. Here, descriptions are given of a case where the change of the observation position is performed by rotating the stage. When an image is taken with, for example, a position of a quadrangle as shown in FIG. 11A used as a viewing field, for example, an imaged shown in a lower part of FIG. 11A is taken. Even in a case where an image corresponding to a different position of the edge is taken, there is no change in the composition of the taken image in which the wafer is shown in the lower part of the display, and in which the background is shown in the upper part thereof. Thus, it is necessary to refer to a map denoted by reference numeral 39 shown in FIG. 9 in order to know the position of an imaged part of the wafer, and it is not possible to intuitively know the position. Then, an image is taken by changing the scanning direction to the one depending on an angle at which the stage is rotated. For example, as shown in FIG. 11B, an area of a wafer edge to be imaged is scanned in a direction tilted at the same angle as the rotation angle θ of the stage. By scanning as is described, an image shown in the lower part of FIG. 11B can be taken. The image has the composition in which a wafer is shown in a lower right part of the image, and in which the background is shown in an upper left part thereof. Thus, it can be intuitively grasped that an image of the upper left part of the wafer edge is taken.

On the other hand, in a case where a beam can be deflected whereby an angle for imaging can be changed, the scanning direction is not necessarily changed, and the same effect can be obtained in the following way. Specifically, without rotating the stage, the stage is moved to a position corresponding to an edge position needing imaging, and then an image thereof is taken with the angle for imaging changed in an arbitrary direction in which the edge is easily observed.

Alternatively, a microscope with an optical system using a wavelength in the range of visible light to ultraviolet light may be also installed, and thus may be used for observing the same position as that to be observed by the electron optical system. With this configuration, instead of obtaining inspection data from the inspection apparatus, a wafer edge is observed in the optical system; the presence of a defect and the position thereof are calculated using a method such as above for determining the presence of defects; the position is recorded; the optical system to be used for observation is switched to the electron optical system; and then the defect position is observed.

What is claimed is:

1. A semiconductor wafer inspection method, the method comprising steps of:

placing a semiconductor wafer on a sample stage of an electron beam apparatus having a first electron beam optical system for irradiating an electron beam from a direction normal to a surface of a sample, and a second electron beam optical system for irradiating an electron beam from a direction tilted from the direction normal to the surface;

obtaining defect position data on the semiconductor wafer from an inspection apparatus;

moving the stage to a position corresponding to a defect position obtained from the defect position data from the inspection apparatus, and capturing a scanning image of a defect by using the first electron beam optical system;

discriminating a mode of the defect on the basis of the captured defect image;

controlling a scanning direction of the electron beam of the second electron beam optical system, wherein the scanning direction of the electron beam of the second electron beam optical system is rotated through an angle the same as a rotation angle of the sample stage so that the viewing field of an image by the second electron beam optical system is rotated through an angle the same as the rotation angle of the stage; and obtaining an image of an edge position of the semiconductor wafer by using the second electron beam optical system, wherein:

the image includes both the edge position of the semiconductor wafer and a background, and altering the rotation angle of the electron beam creates more or less of the background in the image.

2. A defect review apparatus comprising:

a sample stage which moves with a semiconductor wafer held thereon;

a first electron beam optical system for irradiating an electron beam from a direction normal to a surface of the semiconductor wafer held on the sample stage;

a second electron beam optical system for irradiating an electron beam to an edge position of the semiconductor wafer from a direction tilted from the direction normal to the surface;

a display unit for displaying an image of the surface of the semiconductor wafer, the image generated by electron beam irradiation; and a calculation unit configured to:

generate a wafer map showing positions of defects based on images obtained by the first electron beam optical system, and then cause the display unit to display the wafer map superimposing an image obtained by the second electron beam optical system; and an electron optical system control unit configured to:

control a scanning direction of an electron beam from the second electron beam optical system, wherein the scanning direction of the electron beam is rotated through an angle the same as a rotation angle of the sample stage so that the viewing field of an image by the second electron beam optical system is rotated through an angle the same as the rotation angle of the sample stage, wherein:

the image includes both the edge position of the semiconductor wafer and a background, and altering the rotation angle of the electron beam creates more or less of the background in the image.

3. The defect review apparatus according to claim 2, wherein the viewing field of the image obtained by the second electron beam is displayed so as to be superimposed on a wafer map.

\* \* \* \* \*